United States Patent [19]
Gustafson et al.

[11] Patent Number: 4,837,367
[45] Date of Patent: Jun. 6, 1989

[54] LOW PRESSURE CATALYTIC HYDROGENATION OF CARBONYL-CONTAINING COMPOUNDS

[75] Inventors: Bruce L. Gustafson; Paul S. Wehner; Gregory O. Nelson; Patricia N. Mercer, all of Kingsport, Tenn.

[73] Assignee: Eastman Kodak Company, Rochester, N.Y.

[21] Appl. No.: 81,252

[22] Filed: Aug. 3, 1987

[51] Int. Cl.⁴ .................. C07C 31/13; C07C 31/18; C07C 29/136; C07C 29/14

[52] U.S. Cl. .................... 568/831; 568/678; 568/864; 568/862; 568/883; 568/885; 568/861; 568/840

[58] Field of Search ............... 568/831, 864, 885, 678, 568/862, 883, 861

[56] References Cited

U.S. PATENT DOCUMENTS

| | | | |
|---|---|---|---|
| 3,334,149 | 8/1967 | Akin et al. | 260/617 |
| 3,933,930 | 1/1976 | Dougherty et al. | 568/864 |
| 4,105,674 | 8/1978 | De Thomas et al. | 260/343.6 |
| 4,149,021 | 4/1979 | Wall | 568/864 |
| 4,283,581 | 8/1981 | Wilkes | 568/864 |
| 4,398,039 | 8/1983 | Pesa et al. | 560/265 |
| 4,409,395 | 10/1983 | Miyazaki | 560/179 |
| 4,518,714 | 5/1985 | Gustafson | 518/721 |
| 4,628,129 | 12/1986 | Bartley | 568/885 |

FOREIGN PATENT DOCUMENTS

| | | |
|---|---|---|
| 74193 | 3/1983 | European Pat. Off. . |
| 143634 | 5/1985 | European Pat. Off. . |
| 175558 | 3/1986 | European Pat. Off. . |
| 210795 | 2/1987 | European Pat. Off. . |
| 241766 | 10/1987 | European Pat. Off. . |
| 3610698 | 10/1987 | Fed. Rep. of Germany . |
| WO82/03854 | 11/1982 | PCT Int'l Appl. . |
| 879264 | 10/1961 | United Kingdom ............ 568/831 |
| 1534232 | 11/1978 | United Kingdom . |

*Primary Examiner*—Howard T. Mars
*Attorney, Agent, or Firm*—S. E. Reiter; William P. Heath, Jr.

[57] ABSTRACT

Process for the hydrogenation of carbonyl-containing compounds at mild conditions of temperature and pressure to produce alcohols or amines is disclosed, employing palladium on zinc oxide catalysts. A method for the preparation of the palladium on zinc oxide catalysts useful for the desired reductive conversion is also disclosed.

30 Claims, No Drawings

LOW PRESSURE CATALYTIC HYDROGENATION OF CARBONYL-CONTAINING COMPOUNDS

This invention relates to catalytic hydrogenation. In one aspect, the present invention relates to a process for the selective reduction of carbonyl-containing compounds to alcohols. In another aspect, the present invention relates to methods for the preparation of catalysts useful for the selective reduction of carbonyl-containing compounds to alcohols.

BACKGROUND OF THE INVENTION

The catalytic hydrogenation of carbonyl-containing compounds, e.g., esters, to produce their corresponding alcohols, is potentially of great commercial value. Catalysts traditionally employed for such conversions include copper chromite based materials, frequently containing a promoter such as barium. Unfortunately, these catalysts typically require high pressure to achieve commercially attractive reaction rates for the hydrogenation of esters, i.e., pressures in excess of 3000 psig. In addition, chromium and barium present toxicity and environmental concerns which must be dealt with if one is to economically and safely use these materials on a commercial scale.

More recently, substantial amounts of research have been carried out in efforts to develop hydrogenation catalysts capable of reducing carbonyl-containing compounds, e.g., organic acids and esters, to alcohols at reduced pressures. While such catalysts are capable of promoting the hydrogenation of carbonyl-containing compounds to produce alcohols, one problem with such materials is the need to run at very low liquid hourly space velocities in order to achieve suitably high conversion levels.

Another problem frequently encountered with such prior art low pressure catalyst systems when employed for the reduction of carbonyl-containing compounds such as aldehydes and ketones, is their lack of selectivity to the desired alcohol product, such catalysts frequently being too active and thus producing product which results from reaction of substrate with additional hydrogen.

Yet another problem encountered with such prior art low pressure catalyst systems, such as Raney nickel, is the ease of handling of such catalysts, which are frequently pyrophoric, and thus require special handling to avoid fire hazard.

OBJECTS OF THE INVENTION

An object of the present invention, therefore, is a process for the low pressure, high selectivity, high activity hydrogenation of carbonyl-containing compounds to produce alcohols.

Another object of the present invention is a catalyst system which is capable of promoting the hydrogenation of carbonyl-containing compounds at low reaction pressures.

Still another object of the present invention is a catalyst system which is capable of promoting the hydrogenation of carbonyl-containing compounds at low reaction pressure, which catalyst system is readily prepared and requires no special handling precautions.

These and other objects of the present invention will become apparent from inspection of the detailed description and the appended claims which follow.

STATEMENT OF THE INVENTION

In accordance with the present invention, we have discovered that palladium supported on zinc oxide is an effective catalyst for the low pressure hydrogenation of carbonyl-containing compounds to selectively produce alcohols in high yield. The invention process employs readily prepared, easily handled catalysts and enables a commercially important reaction, i.e., the conversion of carbonyl-containing compounds to alcohols, to be carried out at low reaction pressures, thereby reducing the cost of equipment required for the desired hydrogenation reaction and reducing the safety risks involved in such conversions.

DETAILED DESCRIPTION OF THE INVENTION

In accordance with the present invention there is provided a method for preparing high activity, low pressure hydrogenation catalysts comprising palladium on zinc oxide, which method comprises:
  (a) contacting said zinc oxide support or a precursor thereof with palladium or a reducible compound thereof;
  (b) optionally calcining the resulting palladium-treated zinc oxide support or precursor thereof in the presence of an oxygen-containing gas at a temperature in the range of 200° up to 400° C. for a time sufficient to remove substantially all of the counter-ions associated with said palladium or reducible compound thereof and said zinc oxide support or precursor thereof; and
  (c) contacting the optionally calcined palladium-treated zinc oxide support with a reducing atmosphere under conditions sufficient to cause reduction of at least a portion of the palladium to less than the +2 oxidation state.

In accordance with another embodiment of the present invention, there is provided a process for the low pressure hydrogenation of carbonyl-containing compounds of specified structure to produce the corresponding alcohols, which process comprises contacting the carbonyl-containing compounds with a catalyst comprising 0.01 up to 20 weight percent palladium on a zinc oxide-containing support in the presence of hydrogen under hydrogenation conditions.

Catalysts employed in the practice of the present invention comprise palladium on zinc oxide support. A wide variety of techniques for contacting palladium and zinc oxide are suitable. For example, palladium can be applied directly to preformed zinc oxide employing such techniques as incipient wetness, wet impregnation, metal atom evaporation, precipitation, or appropriate precursors of palladium and zinc can be coprecipitated, then calcined to remove the counter ions introduced by the precursor compounds, and, finally, reduced to convert the palladium to an active form.

A wide range of zinc compounds are suitable zinc oxide precursors for use in the practice of the present invention, e.g., zinc nitrate, zinc halides, zinc acetate, zinc carbonate, and the like. Similarly, a variety of zinc oxide compounds can be directly employed as catalyst support. Typically, such preformed zinc oxide materials will contain an impurity content no greater than about 5%. Preferred zinc oxide compounds will contain at least 60% zinc oxide by weight, with up to 40% by weight of inert materials such as:
    $SiO_2$, Al₂O₃, and
TiO₂
being employed as inert diluents and as catalyst binders.

The surface area of the catalyst supports employed can vary widely. Preferably, support materials employed in the practice of the invention will have surface areas of at least about 1 m²/g. Of course, those of skill in the art also recognize that higher surface area materials will generally produce higher activity catalysts than lower surface area catalysts having comparable composition.

When zinc oxide is prepared by calcination of a precipitated zinc oxide precursor, temperatures in the range of about 200° up to 400° C. are generally employed. Such temperature is maintained for a time sufficient to remove substantially all the counter ions introduced by the zinc oxide precursor (and the palladium compound employed) to form the catalyst. Times in the range of about 2 up to 8 hours or longer are generally effective for this purpose.

Suitable sources of palladium are any compounds which are reducable when subjected to reducing conditions. Since many palladium compounds are convertible to the oxide form upon calcination under the above-described conditions, and the oxides of palladium are readily reduced, many palladium compounds are useful for catalyst preparation. Exemplary palladium compounds include the palladium halides, palladium acetate, palladium nitrate, palladium ammine complexes, organometallic complexes of palladium, and the like.

The term "carbonyl-containing compounds" as employed in this specification is intended to include compounds of the structure

wherein
R is a C₁-C₂₀ alkyl or substituted alkyl radical; or a C₂-C₂₀ alkenyl or alkynyl radical or substituted derivative thereof;
wherein said substituted groups include ethers, amines, additional carbonyl groups, aryl groups, hydroxyl groups and alkoxy groups; and
Z=H,
R', wherein R' is defined the same as R, and is selected independently of R,
OR', wherein R' is as defined above,
X, wherein X is any one of the halogens,
NR"₂, wherein each R" is independently selected from H or R';
with the proviso that R and Z can be joined as part of a polymethylene or hydrocarbyl- or heteroatom-substituted polymethylene radical, poly-carbonyl analogs of such carbonyl-containing compounds; and mixtures of any two or more thereof.

Preferred carbonyl-containing compounds are compounds selected from the group consisting of:

YO₂C—A—CO₂Y,   (a)

wherein A is an alkylene moiety, an alkenylene moiety, or an alkynylene moiety having 1 up to 20 carbon atoms, or substituted derivative thereof, or a cycloalkyl ior cycloalkenyl moiety having 4-12 carbon atoms or substituted derivative thereof; and wherein each Y is independently a C₁ up to C₁₂ alkyl, alkenyl or alkynyl radical or substituted derivative thereof;

B—CO₂Y   (b)

wherein B is an alkyl, alkenyl or alkynyl radical, or substituted derivative thereof, having 1 up to 20 carbon atoms; and wherein Y is defined as above;

wherein Z is an alkyl, alkenyl or alkynyl radical having 1 up to 20 carbon atoms or substituted derivatives thereof; and mixtures of any two or more thereof.

Exemplary carbonyl-containing compounds which satisfy the above formulae include alkyl oleates, dialkyl adipates, propionaldehyde, dialkyl cyclohexane dicarboxylates, alkyl acrylates, alkyl propionates, alkyl isobutyrates, alkyl normal butyrates, alkyl acetates, nonanal, dialkyl butane dicarboxylates, alkyl methacrylates, alkyl crotonates, alkyl isocrotonates, alkyl sorbates, alkyl cinnamates, maleic anhydride, alkyl fumarates, dialkyl succinates, succinic anhydride, alkyl glutarates, dialkyl malonates, dialkyl octanedioates, dialkyl decanedioates, dialkyl dodecanedioates, alkyl laurates, alkyl myristates, alkyl palmitates, alkyl stearates, alkyl linoleates, alkyl linolenates, alkyl isovalerates, alkyl normal valerates, alkyl caproates, alkyl caprylates, alkyl 2-ethylhexanoates, dialkyl cyclohexanedioates, γ-butyrolactone, alkyl phenylacetates, alkyl cyclohexane carboxylates, alkyl pyruvates, alkyl glycolates, alkyl oxalates, alkyl formates, alkyl lactates, alkyl citrates, glyceride esters, and the like.

Typical alkyl groups employed have from 1 up to 20 carbon atoms, with alkyl groups having 1 up to 6 carbon atoms being preferred.

The hydrogenation process of the present invention involves contacting at least one of the above-described carbonyl-containing compounds with at least one of the above-described palladium/zinc oxide catalysts in the presence of hydrogen under hydrogenation condtions. Hydrogenation conditions typically employed in the practice of the present invention are set forth below.

The process of the present invention can be operated in a variety of configurations. Depending on the substrate to be hydrogenated, the preferred method of opeation is frequently in a fixed bed flow reaction system. If the vapor pressure of the substrate to be hydrogenated is sufficiently high at reaction temperature, the desired method of operation may be vapor phase, i.e., all reactants and products exist in the gaseous phase. For other substrates, the desired method of operation may be a trickle bed configuration. Regardless of the method of operation, the desired time of contact between the reactants and catalyst components can be varied s desired to achieve the desired level of reaction.

In typical fixed bed operation, pressures in the range of 100–10,000 psig will be employed. Preferably, the pressure will be in the range of 100–2500 psig. Similarly, temperatures in the range of 25°–400° C. can be used, with a more preferred range of 100°–290° C. While the feed rate of the substrate will be varied to control the level of conversion, normal liquid hourly space velocities (LHSV) will be in the range of about 0.01–100 h⁻¹, with a preferred range of 0.1–20 h⁻¹. The molar ratio of hydrogen to substrate will typically be in the range of 1:1 to 1000:1 with a preferred range of 2:1 to 100:1.

Alternatively the invention may be conducted in a slurry phase reactor. In slurry phase operation, the ratio of carbonyl-containing compound to catalysts employed can vary widely, with ratios as low as 1:1 or lower being operable, but not economically attractive; and ratios as high as 10,000:1 and higher also being operable, but generally providing relatively low conversions unless very long contact times are employed. Preferred carbonyl-containing compound:catalysts ratios fall within the range of about 1:1 up to 1,000:1, with ratios in the range of about 2:1 up to 100:1 being most preferred because good levels of conversion of the carbonyl-containing compounds are obtained without requiring excessive amounts of catalysts, or extremely long contact times.

While the invention hydrrogenation process can be carried out in the absence of solvent, it is presently preferred to perform the process in the presence of a suitable solvent. Suitable solvents are compounds which are fluid and in which the carbonyl-containing starting material is soluble at reaction temperature, and which are non-reactive under hydrogenation conditions. Preferred solvents are those which are fluid and in which the carbonyl-containing starting material is soluble at room temperature. Exemplary solvents include aromatic solvents such as toluene; alcohols such as methanol; ethers such as diphenyl ether and tetrahydrofuran; and the like.

When employed, the volume/volume ratio of solvent to substrate can vary widely, typically falling in the range of about 5:95 to 95:5.

In a preferred embodiment of the present invention, hydrogenation of carbonyl-containing compounds is carried out with small amounts of water (i.e., 0.01 up to about 2 wt. % water based on the total weight of reactants and solvent) present in the reaction mixture. It has been found that selectivity to hydrogenation (as opposed to transesterification between reactant and product) products is greatly improved by the presence of such small quantities of water in the reaction mixture.

Following hydrogenation, the desired product can be recovered and purified using conventional techniques well known to those of skill in the art. For example, catalysts can be removed from the reaction mixture by filtration, decantation and the like. By-products and unreacted starting material as well as solvent, if employed, can be separated from the product by distillation, recrystallization, solvent/solvent extraction, and the like.

The invention will now be described in greater detail by reference to the following non-limiting examples.

EXAMPLE 1

Catalyst Preparation

A sample of 1 wt % Pd supported on ZnO was prepared as follows: A solution of Pd was prepared by dissolving 20 g of $Pd(NO_3)_2$ in 50 ml of $H_2O$ and 16 g of $HNO_3$. This solution was diluted to 750 ml and added to 925 g of powdered ZnO. The resulting mixture was heated at 90° C. in air until dry. The sample was then calcined at 200° C. for two hours prior to catalytic evaluation. Approximately 1 cc of powdered sample was loaded into a plug flow microreactor and heated to 300° C. in flowing hydrogen. The catalyst was held at 300° C. for two hours prior to evaluation for hydrogenation of carbonyl-containing compounds.

EXAMPLE 2

Methyl Acetate Hydrogenation; Effect of Water in the Feed

Catalyst prepared as described in Example 1 was employed for the vapor phase hydrogenation of methyl acetate. All evaluations were conducted using a hydrogen/ester ratio of 4.0 and a gas hourly space velocity (GHSV; volume of gas/volume of catalyst/hr) of 30,180 $hr^{-1}$. The effect of water content in the feed is demonstrated by the results presented in Table I.

TABLE I

| Catalytic Hydrogenation over Pd/ZnO | | | | | |
|---|---|---|---|---|---|
| Run # | Temp., °C. | Pressure, psig | wt % $H_2O$ | Rate ($\mu$moles/g-cat sec)* MeOH | EtOH | EtOAc |
| 1 | 298 | 730 | 0.0 | 7.3 | 2.0 | 3.6 |
| 2 | 298 | 720 | 0.1 | 4.3 | 2.4 | 1.8 |
| 3 | 298 | 720 | 0.5 | 2.8 | 1.5 | 0.3 |
| 4 | 296 | 725 | 1.0 | 1.5 | 1.1 | 0.1 |

*MeOH = methanol
EtOH = ethanol
EtOAc = ethyl acetate

The results set forth in Table I demonstrate that the addition of small amounts of water to the reaction mixture promotes improved catalyst performance by reducing the occurrence of undesired transesterification by-product formation.

EXAMPLE 3

Hydrogenation of Methyl Acetate

Catalyst prepared as described in Example 1 was evaluated in the manner described in Example 2. The water content of the feed was approximately 1% by weight for all of the runs carried out. Results from these evaluations are presented in Table II.

TABLE II

| Catalytic Evaluation of Pd/ZnO Methyl Acetate Hydrogenation | | | | | | |
|---|---|---|---|---|---|---|
| Run # | Temp., °C. | Press., psig | $H_2$/Ester, moles | Rate ($\mu$moles/g-cat sec)* MeOH | EtOH | EtOAc |
| 5 | 296 | 570 | 0.34 | 2.1 | 1.4 | <0.01 |
| 6 | 295 | 735 | 0.34 | 2.5 | 1.8 | 0.05 |
| 7 | 307 | 980 | 0.15 | 7.1 | 5.9 | 0.7 |
| 8 | 333 | 735 | 3.97 | 11.0 | 9.0 | 0.8 |

*MeOH = methanol
EtOH = ethanol
EtOAc = ethyl acetate

The results set forth in Table II demonstrate that Pd/ZnO catalyst is effective for the conversion of esters with high selectivity to the corresponding alcohols at pressures below 1000 psig. In addition, excellent catalyst performance is obtained under a variety of the reactiion parameters, i.e., temperature, pressure and feed composition.

EXAMPLE 4

Hydrogenation of Methyl Propionate

The catalyst prepared as described in Example 1 was evaluated in the same manner as described in Example 2 for the hydrogenation of methyl propionate. Reaction parameters and results from this evaluation are given below.

| Temperature | 333° C. | |
| Pressure | 710 psig | |
| H$_2$/ester | 4.8 | |
| GHSV | 29,178 h$^{-1}$ | |
| Conversion | 16.% | |
| | methanol | propanol |
| Rate ($\mu$moles/g-cat sec): | 12. | 9.0 |

These results demonstrate that Pd/ZnO is an effective catalyst for the hydrogenation of methyl propionate to propanol and methanol. Note the very high reaction rates obtained even under non-optimized reaction conditions.

EXAMPLE 5

Hydrogenation of Methyl n-Butyrate

The catalyst prepared as described in Example 1 was evaluated in the same manner as described in Example 2 for the hydrogenation of methyl n-butyrate. Reaction parameters and results from this evaluation are given below.

| Temperature | 333° C. | |
| Pressure | 725 psig | |
| H$_2$/ester | 5.6 | |
| GHSV | 28,410 h$^{-1}$ | |
| Conversion | 17.% | |
| | methanol | n-butanol |
| Rate ($\mu$moles/g-cat sec): | 5.9 | 6.1 |

The results demonstrate that Pd/ZnO is an effective catalyst for the hydrogenation of methyl n-butyrate to n-butanol and methanol.

EXAMPLE 6

Hydrogenation of Methyl i-Butyrate

The catalyst prepared as described in Example 1 was evaluated in the same manner as described in Example 2 for the hydrogenation of methyl i-butyrate. Reaction parameters and results from this evaluation are given below.

| Temperature | 334° C. | |
| Pressure | 725 psig | |
| H$_2$/ester | 5.7 | |
| GHSV | 28,372 h$^{-1}$ | |
| Conversion | 25.% | |
| | methanol | i-butanol |
| Rate ($\mu$moles/g-cat sec): | 2.9 | 6.0 |

These results demonstrate that Pd/ZnO is an effective catalyst for the hydrogenation of methyl i-butyrate to i-butanol and methanol. Even under these non-optimized reaction conditions, the per pass conversion was 25%.

EXAMPLE 7

Hydrogenation of Ethyl Acetate

The catalyst prepared as described in Example 1 was evaluated in the same manner as described in Example 2 for the hydrogenation of ethyl acetate. Reaction parameters and results from this evaluation are given below.

| Temperature | 332° C. |
| Pressure | 725 psig |

-continued

| H$_2$/ester | 4.9 |
| GHSV | 29,100 h$^{-1}$ |
| Conversion | 16.% |
| | Ethanol |
| Rate ($\mu$moles/g-cat sec): | 16.7 |

These results demonstrate that Pd/ZnO is an effective catalyst for the hydrogenation of ethyl acetate to ethanol. Note the high selectivity and very high rate of reaction even under these non-optimized conditions.

EXAMPLE 8

Hydrogenation of 1,4-Dimethylcyclohexane Dicarboxylate

A catalyst was prepared in the same manner as described in Example 1. For catalytic evaluation, 260 cc of catalyst (14×40 standard mesh particles) was loaded into a 1 inch fixed bed reactor. The sample was treated in a hydrogen flow while heating the catalyst to reaction temperature. The system pressure was then increased to the desired reaction pressure. The ester feed consisted of 10 wt% 1,4-dimethylcyclohexane dicarboxylate (DMCD) in 1-dodecanol. Catalytic evaluation was conducted using a liquid feed rate of 80 g/h, 290° C., 1250 psig, and a 1000 standard cubic centimeters (sccm) hydrogen flow. Under these conditions, the DMCD conversion was 93.3%. The observed products were 60 mol % cyclohexanedimethanol (CHDM) and 40 mole % 1-methyl, 4-dodecyl, cyclohexanedicarboxylate.

The above-described catalyst and reaction set-up were employed in the same manner as described except that the reaction conditions were changed to a liquid feed rate of 13 g/h, 300° C., 1250 psig, and 130 sccm hydrogen. Under these conditions, the observed conversion of DMCD was 99.5% with 93.3% molar selectivity to CHDM.

These results demonstrate that Pd/ZnO is a very effective catalyst for the selective hydrogenation of DMCD to CHDM.

EXAMPLE 9

Effect of Support Surface Area on Catalyst Performance

Catalyst samples were prepared as described in Example 1 except that various sources of ZnO were used for the catalyst support.

TABLE III

Catalytic Evaluation of Pd/ZnO
Methyl Acetate Hydrogenation
Temperature 300° C.
Pressure 720 psig
H$_2$/Ester 4.0
Water 1 wt %

| Run # | ZnO Source | BET Surface Area, m$^2$/g | Rate ($\mu$moles/g-cat sec)* | | |
|---|---|---|---|---|---|
| | | | MeOH | EtOH | EtOAc |
| 15 | A | 3.3 | 3.0 | 2.4 | 0.2 |
| 16 | B | 4.7 | 2.8 | 2.0 | 0.2 |
| 17 | C | 4.3 | 2.8 | 2.3 | 0.1 |
| 18 | D | 27.0 | 6.0 | 5.8 | 0.4 |

*MeOH = methanol
EtOH = ethanol
EtOAc = ethyl acetate

These results demonstrate that a variety of zinc oxide-containing support materials are useful supports for the Pd/ZnO catalyst of the present invention. In addition, the results show that the rate of reaction with Pd/ZnO catalyst is greatly improved with higher surface area support.

EXAMPLE 10

Catalyst with Modified Catalyst Support: $ZnO/Al_2O_3$ $ZnO/Al_2O_3$ was prepared by dissolving 365 g of zinc nitrate in 800 ml of water at 60° C. A solution of $Na_2CO_3$ (160 g/700 ml) was slowly added to the Zn solution while stirring to precipitate the Zn. The resulting precipitate was washed in 1000 ml of water, filtered and dried at 90° C. The resulting solid was heated in a flow of air at 350° C. for four hours. A portion of this solid (50 g) was added to 32 g of aluminum hydrate and 200 ml of water. This mix was blended for 20 minutes, filtered, and finally heated in a flow of air at 350° C. for four hours. The resulting powder had a BET surface area of 79 $m^2/g$. The final Pd/ZnO, $Al_2O_3$ catalyst was prepared by adding an aqueous solution containing 0.24 g of Pd nitrate to 10 g of the $ZnO/Al_2O_3$ support material, drying the resulting mixture at 90° C., and then heating in a flow of air at 250° C. for four hours.

The catalyst was evaluated for methyl acetate hydrogenation activity as described in Example 2. The reaction parameters employed and results obtained were as follows:

| Temperature | 332° C. |
|---|---|
| Pressure | 720 psig |
| $H_2$/ester | 4.1 |
| Wt % $H_2O$ | 0.0 |
| GHSV | 30,180 $h^{-1}$ |
| Methyl Acetate conversion | 12.0% |
| Product | Rate ($\mu$moles/g-cat sec) |
| $CH_3OH$ | 21.4 |
| $CH_3CH_2OH$ | 5.6 |
| $CH_3CO_2CH_2CH_3$ | 8.8 |

These results indicate that alumina can be added to the preparation of invention catalyst, if desired. It is of note that high selectivity to the desired hydrogenation products, methanol and ethanol, are obtained even at the high rates of reaction achieved with the Pd/ZnO-$Al_2O_3$ catalyst.

EXAMPLE 11

Diethyl Adipate Hydrogenation

A hydrogenation reaction was conducted as described in Example 8 except that diethyl adipate was used in place of DMCD and the catalyst volume was 100 cc. Operation conditions are given below:

| Temperature | 300° C. |
|---|---|
| Pressure | 1233 psig |
| $H_2$ Feed Rate | 760 sccm |
| Liquid Feed Rate | 189 ml/hr |

Analyses of the liquid product stream gave the following results:

| Dodecyl alcohol | 92% |
|---|---|
| Diethyl adipate | 2.2% |
| 1,6-hexandiol | 2.8% |
| $C_6^+$ products | 3.% |

The results show that Pd/Zno is effective for the conversion of dibasic esters such as diethyl adipate to the corresponding diol.

EXAMPLE 12

Methyl Oleate Hydrogenation

Hydrogenation of methyl oleate was carried out as described in Example 11 except that the liquid feed contained pure methyl oleate. The liquid feed rate was 68 ml/hr and the reaction temperature was 290° C. Analysis of the product mixture gave the following results.

| Methyl oleate | 4.1 wt % |
|---|---|
| Stearyl Alcohol | 42 wt % |
| Oleyl Alcohol | 50 wt % |

These results demonstrate the utility of Pd/ZnO for the conversion of methyl oleate to a mixture of C-18 alcohols at low pressure. Of particular note is the fact that a significant portion of the hydrogenation product is the unsaturated product, oleyl alcohol. Isolation of this product is particularly noteworthy in view of the fact that the material has been subjected to reducing conditions in the presence of a catalytic material (i.e., Pd) which is generally quite effective for double bond hydrogenation. Thus, hydrogenation in accordance with the present invention is seen to be selective for reduction of carbon-oxygen double bonds (i.e., carbonyl bonds) relative to carbon-carbon double bonds.

EXAMPLE 13

Hydrogenation of Propionaldehyde

A Pd/ZnO catalyst prepared as described in Example 1 was evaluated for the vapor phase hydrogenation of propionaldehyde in a micro reactor system. Approximately 1 cc of catalyst was charged to the reactor and pretreated as described in previous examples. The reaction parameters employed and results obtained were as follows:

| Temperature | 130° C. |
|---|---|
| Pressure | 800 psig |
| $H_2$/Aldehyde | 4.0 |
| GHSV | 30,000 $h^{-1}$ |
| Propionaldehyde conversion | 49.0% |
| Product | Selectivity, wt % |
| $CH_3CH_2CH_2OH$ | 45 |
| 2-methyl-2-pentenal | 55 |

The results demonstrate the utility of Pd/ZnO catalyst for the conversion of propionaldehyde to propanol.

EXAMPLE 14

Hydrogenation of Nonanal

A 1% Pd on ZnO catalyst prepared as described in Example 1 was evaluated for the slurry phase hydrogenation of nonanal. Nonanal (4 g) was mixed with toluene (75 ml) and 1% Pd/ZnO (1 g). This mixture was placed in a stirred autoclave and heated to 100° C. under 100 psig hydrogen pressure. The system was pressurized to 1500 psig and the mixture stirred for two hours. The autoclave was then cooled, vented and the resulting product mixture analyzed by gas chromatography (GC). For the comparative example, 1 g of a commercially available 1% Pd/Al$_2$O$_3$ was substituted for the Pd/ZnO catalyst. The results were as follows:

| Catalyst | GC Analysis, wt % | | |
|---|---|---|---|
|  | Nonanal | Nonanol | Unknown |
| 1% Pd/ZnO | 0.9 | 99. | 0.0 |
| 1% Pd/Al$_2$O$_3$ | 28.7 | 60.2 | 11.1 |

Pd/ZnO exhibits substantially higher activity and selectivity than Pd/Al$_2$O$_3$ under identical conditions for the hydrogenation of nonanal.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A process for the low pressure hydrogenation of carbonyl-containing compounds to produce the corresponding alcohol, wherein said carbonyl-containing compounds have the structure:

$$R-\overset{\overset{O}{\|}}{C}\diagdown Z$$

wherein

R is a C$_1$-C$_{20}$ alkyl or substituted alkyl radical; or a C$_2$-C$_{20}$ alkenyl or alkynyl radical or a substituted derivative thereof;

wherein said substituted groups are selected from the group consisting of additional carbonyl groups, aryl groups, hydroxyl groups and alkoxy groups; and Z is selected from the group consisting of: H and OR' wherein R' is defined the same as R, and is selected independently of R, with the proviso that R and Z can be joined as part of a polymethylene or hydrocarbyl-substituted polymethylene radical; and mixtures of any two or more thereof; said process comprising contacting said carbonyl-containing compounds with a catalyst comprising 0.01 up to 20 wt % palladium on a zinc oxide-containing support in the presence of hydrogen under hydrogenation conditions.

2. A process in accordance with claim 1 wherein said contacting is carried out in the further presence of in the range of 0.01 up to 2.0 wt % water, based on the total weight of reactants and solvent charged to the reactor.

3. A process in accordance with claim 1 wherein said catalyst is prepared by:
   (a) contacting said zinc oxide support or a precursor thereof with palladium or a reducible compound thereof; and
   (b) contacting the palladium-treated zinc oxide support with a reducing atmosphere under conditions sufficient to cause reduction of at least a portion of the palladium to less than the +2 oxidation state.

4. A process in accordance with claim 3 further comprising calcining the palladium-treated zinc oxide support or precursor thereof produced in step (a) in the presence of an oxygen-containing gas at a temperature in the range of 200° up to 400° C. for a time sufficient to remove substantially all of the counter ions associated with said palladium or reducible compound thereof and said zinc oxide support or precursor thereof, prior to said contacting with a reducing atmosphere.

5. A process in accordance with claim 1 wherein said hydrogenation conditions comprise a temperature in the range of 25° up to 400° C., and a pressure in the range of 100 up to 10,000 psig.

6. A process in accordance with claim 5 wherein the hydrogen partial pressure falls within the range of 100 up to 10,000 psig.

7. A process in accordance with claim 5 wherein said hydrogenation conditions comprise a temperature in the range of 100° up to 290° C. and a pressure in the range of 100 up to 2500 psig.

8. A process in accordance with claim 1 wherein the liquid hourly space velocity falls within the range of about 0.01 up to 100 h$^{-1}$.

9. A process in accordance with claim 1 wherein the weight ratio of carbonyl-containing compound to catalyst falls within the range of 1:1 up to 10,000:1.

10. A process in accordance with claim 1 wherein the carbonyl-containing compound is selected from the group consisting of:

$$YO_2C-A-CO_2Y, \qquad (a)$$

wherein A is an alkylene moiety, an alkenylene moiety, or an alkynylene moiety having 1 up to 20 carbon atoms, or substituted derivative thereof, or a cycloalkyl or cycloalkenyl moiety having 4–12 carbon atoms or substituted derivative thereof; and wherein each Y is independently a C$_1$ up to C$_{12}$ alkyl, alkenyl or alkynyl radical or substituted derivative thereof;

$$B-CO_2Y \qquad (b)$$

wherein B is an alkyl, alkenyl alkynyl radical, or substituted derivative thereof, having 1 up to 20 carbon atoms; and wherein Y is defined as above;

$$Z-\overset{\overset{O}{\|}}{C}-H \qquad (c)$$

wherein Z is an alkyl, alkenyl or alkynyl radical having 1 up to 20 carbon atoms or substituted derivatives thereof; and mixtures of any two or more thereof.

11. A process in accordance with claim 10 wherein the carbonyl-containing compound comprises a dialkyl adipate.

12. A process in accordance with claim 11 wherein said alkyl radical has in the range of 1 up to 6 carbon atoms.

13. A process in accordance with claim 10 wherein the carbonyl-containing compound comprises a dialkyl cyclohexanedicarboxylate.

14. A process in accordance with claim 13 wherein said alkyl radical has in the range of 1 up to 6 carbon atoms.

15. A process in accordance with claim 10 wherein the carbonyl-containing compound is selected from the group consisting of an alkyl oleate, an alkyl stearate, an alkyl linoleate, an alkyl linolenate, an alkyl α-eleostearate, an alkyl β-eleostearate, and mixtures of any two or more thereof.

16. A process in accordance with claim 15 wherein said alkyl radical has in the range of 1 up to 6 carbon atoms.

17. A process in accordance with claim 10 wherein the carbonyl-containing compound comprises a dialkyl butanedicarboxylate.

18. A process in accordance with claim 17 wherein said alkyl radical has in the range of 1 up to 6 carbon atoms.

19. A process in accordance with claim 10 wherein the carbonyl-containing compound comprises a glycerol ester.

20. A process in accordance with claim 19 wherein said alkyl radical has in the range of 1 up to 6 carbon atoms.

21. A process in accordance with claim 10 wherein the carbonyl-containing compound comprises a dialkyl glutarate.

22. A process in accordance with claim 21 wherein said alkyl radical has in the range of 1 up to 6 carbon atoms.

23. A process in accordance with claim 10 wherein the carbonyl-containing compound is selected from the group consisting of dialkyl fumarates, succinates, maleates, and mixtures of any two or more thereof.

24. A process in accordance with claim 23 wherein said alkyl radical has in the range of 1 up to 6 carbon atoms.

25. A process in accordance with claim 10 wherein the carbonyl-containing compound comprises an alkyl decanoate.

26. A process in accordance with claim 25 wherein said alkyl radical has in the range of 1 up to 6 carbon atoms.

27. A process in accordance with claim 10 wherein the carbonyl-containing compound comprises an alkyl dodecanoate.

28. A process in accordance with claim 27 wherein said alkyl radical has in the range of 1 up to 6 carbon atoms.

29. A process in accordance with claim 10 wherein the carbonyl-containing compound is selected from the group consisting of alkyl acetates, propionates, butyrates, valerates, caproates, and mixtures of any two or more thereof.

30. A process in accordance with claim 20 wherein said alkyl radical has in the range of 1 up to 6 carbon atoms.

* * * * *